United States Patent [19]

Lindoerfer et al.

[11] Patent Number: 4,921,615

[45] Date of Patent: May 1, 1990

[54] SEPARATION OF SOLID PARTICLES OF VARIOUS SIZES FROM VISCOUS LIQUIDS

[75] Inventors: Walter Lindoerfer, Kassel; Kai-Udo Sewe, Barnstorf; Wilhelm Jahn-Held, Staufenberg; Burkhard Ziebolz, Braunschweig; Fritz Wagner, Braunschweig-Stoeckheim, all of Fed. Rep. of Germany

[73] Assignee: Wintershall AG, Kassel, Fed. Rep. of Germany

[21] Appl. No.: 199,863

[22] Filed: May 27, 1988

[30] Foreign Application Priority Data

May 27, 1987 [DE] Fed. Rep. of Germany ....... 3717902

[51] Int. Cl.$^5$ .............................................. B01D 37/08
[52] U.S. Cl. .................................... 210/729; 210/774; 210/806; 210/808
[58] Field of Search ................ 210/807, 264, 290–293, 210/317, 335, 350–352, 484, 489–492, 496, 499, 729, 737, 741, 742, 774, 806, 808

[56] References Cited

U.S. PATENT DOCUMENTS

| | | | |
|---|---|---|---|
| 3,865,758 | 2/1975 | Yoshida et al. | 210/496 X |
| 4,039,448 | 8/1977 | Etani | 210/496 X |
| 4,162,216 | 7/1979 | Nyer | 210/807 X |
| 4,246,107 | 1/1981 | Takenaka et al. | 210/317 X |
| 4,569,756 | 2/1986 | Klein | 210/496 X |
| 4,640,778 | 2/1987 | Blomback et al. | 210/484 |

OTHER PUBLICATIONS

Ullmanns Encyclopadie der Techn. Chemie, 4 Auflage, Band 2, pp. 156–157.

*Primary Examiner*—Tom Wyse
*Attorney, Agent, or Firm*—Keil & Weinkauf

[57] ABSTRACT

Solid particles of various sizes are separated from viscous liquids, for example biomass from liquids of biotechnological processes, by pressure filtration by subjecting the inhomogeneous or homogenized suspension, without or after only a little dilution, to a pressure filtration whereby the solid particles of various sizes are retained according to size in a plurality of, in particular in from 1 to 3, superposed or juxtaposed filter stages on filter layers of various depths and on filter surfaces and are separated from the viscous liquid.

23 Claims, 1 Drawing Sheet

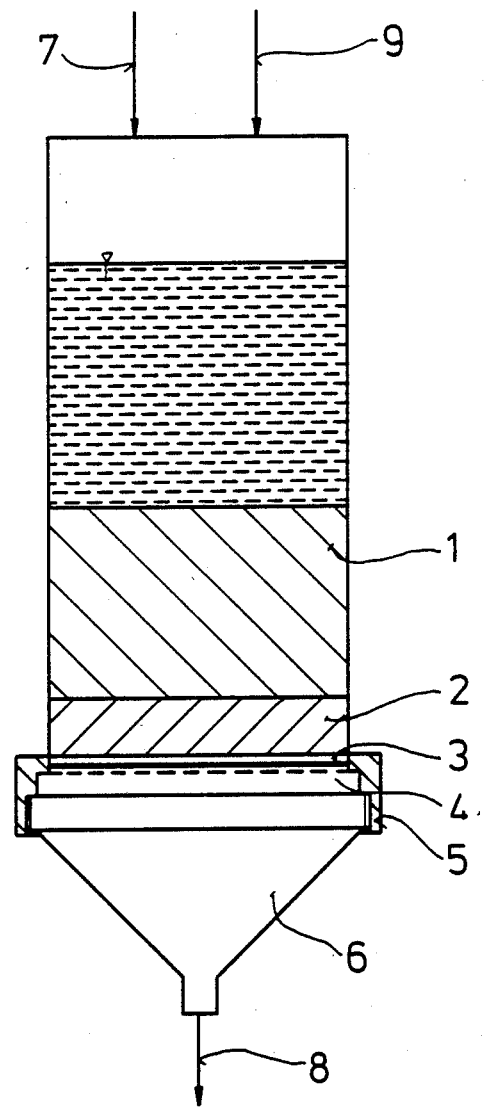

SEPARATION OF SOLID PARTICLES OF VARIOUS SIZES FROM VISCOUS LIQUIDS

The present invention relates to a process for separating solid particles of various sizes from viscous liquids, for example biomass from liquids of biotechnological processes, by pressure filtration.

In the workup of viscous polysaccharide solutions from biotechnological processes, a fundamental problem has to be overcome, namely to separate the biomass from the viscous liquid phase. In the case of the polysaccharide, a B-D-1,3-glucan, formed by fungus of strain ATCC 15205, there are additional problems due to the fact that a not inconsiderable proportion of the product adheres to the mycelium and is structurally similar to cell wall constituents.

The raw culture broth has hitherto been worked up by strongly diluting it, then filtering the dilute culture broth through conventional filter material, or centrifuging it, and reconcentrating the filtrate. In this sequence of operations, the dilution step is indispensable since the undiluted culture broth (an inhomogeneous mixture of mycelium, polysaccharide, media constituents and water) very quickly blocks up any conventional filter medium ever investigated or, owing to the high viscosity, renders sedimentation of the biomass through centrifugation impossible. Nor is it possible to separate the culture broth in a two-phase system owing to the structural similarity between the product and the cell wall.

Despite dilution, the lifetimes of membranes employed in the filtrations mentioned are only short. Nor does the prior art disclose a more effective process without higher hardware requirements.

It is an object of the present invention, starting from the prior art as represented in Ullmann's Encyclopädie der Technischen Chemie, 4th edition, volume 2, pages 156/157, to separate the biomass from ideally undiluted, raw culture broths.

We have fond that this object is achieved according to the invention by subjecting the inhomogeneous or homogenized suspension, without or only after a little dilution, to a pressure filtration whereby the solid particles of various sizes are retained according to size in a plurality of in particular in from 1 to 3, superposed or juxtaposed filter stages on filter layers of various depths and on filter surfaces and are separated from the viscous liquid.

Further features of the invention form the subject-matter of the subclaims.

In this pressure filtration, the pressure is exerted on the gas phase above the liquid to be filtered or directly on the liquid phase and is in the range from 1 to 10 bar. The filter layers for separating off coarse particles consist of a three-dimensional network of metal wire or synthetic cloth or cellulose material having an average pore width of from 1 to 3 mm and of sufficient depth (from 10 to 100 mm). For example, the density of such a synthetic filter is up to 80 kg/m$^3$, while that of the metal version is correspondingly higher.

To separate off relatively fine particles the next stage comprises for example an open-pored polyurethane foam (average pore width from 0.2 to 0.8 mm, density up to 80 kg/m$^3$), followed finally for example by silk gauze (mesh size from 0.006 to 0.2 mm) or similar filter surfaces made of natural or synthetic materials. The pore width of the foam can be reduced in size by compressing the foam.

This filter technique is a combination of depth and surface filtration. In the upper filter layers first encountered by the flowing medium, the biomass is retained inside the filter, while at the silk gauze and similar filter cloths the pretreated suspension is subjected to a surface filtration.

The filter apparatus should be constructed in such a way as to maximize the size of the filter area. The flow on the inside must be influenced by constructional measures in such a way that the suspension cannot escape from passing through the filter layers.

This system is flexible and, by proper selection of the filter layers, is adaptable to different problem situations. The system has proved to be of good utility in particular in the case of highly inhomogeneous culture broths of high mycelium content (up to 10 g of dry matter/l) and high polymer concentrations (up to 12 g of dry matter/l) as obtained from shaking flask cultivations.

It will be readily understood that the process can also find utility in other fields where viscous liquids are worked up, as for example in the
- production of celluloid
- production of cellulose ethers
- production of cellulosic fibers
- production of fats and oils
- production of gelatin
- production of natural and synthetic resins
- production of adhesives and sealants
- production of pectin
- production of starch
- production of lubricants
- production of other polysaccharides (agar, alginate, carrageen, dextran).

In what follows, the process according to the invention is further illustrated by reference to a drawing and to various Examples.

The drawing shows a section through a laboratory pressure filter unit used for filtering the various culture broths.

In the pressure filter unit, three different filter layers 1, 2 and 3 are arranged one below the other in the direction of flow or in certain circumstances even side by side. As in existing apparatus these filter layers are arranged on top of a filter support unit 4, into which position they are inserted from below. A coupling ring 5 connects the conical filter outlet 6 to the pressure filter unit and at the same time ties the filter support unit firmly into the pressure filter unit. The culture broth is fed in via line 7 and the filtrate is discharged via line 8. Line 9 is used to supply air or inert gas to apply the necessary pressure on the gas phase above the culture broth or directly on the culture broth. The pressure filter construction described permits rapid and easy replacement of the filter layers; however, this is also true of existing apparatus and not relevant to the invention. Conveniently, two pressure filter units are disposed in a parallel arrangement, so that there is always one unit in operation while at the same time in the other unit the filter layers are cleaned or replaced. It is also technically advantageous to clean the filter stages by back flushing.

EXAMPLE 1

Three-stage pressure filtration of viscous, inhomogeneous cell suspension

A viscous, aqueous cell suspension obtained by culturing of *Sclerotium rolfsii* ATCC 15 205 has the following composition:

Inhomogeneous cell size distribution 0.005 m (hyphae fragments up to 1 cm pellets) in diameter:

| | |
|---|---|
| cell dry matter: | 4.53 g/l |
| homoglucan content of aqueous solution: | 5.12 g/l |
| viscosity of cell suspension: | about 1200 mPas at a shear rate of $D = 9s^{-1}$ at 20° C. |

1 liter of this cell suspension is introduced into the pressure filter unit shown in the drawing and is subjected to a pressure filtration at 20° C. under a positive pressure of 3 bar.

Filter structure

| | |
|---|---|
| Filter stage 1: | Three-dimensional synthetic cloth having an average pore width of 2 mm and a depth of 40 mm |
| Filter stage 2: | Polyurethane foam (density: 60 kg/m³, pore width: 0.55 mm, depth: 10 mm) |
| Filter stage 3: | Silk gauze (pore width: 0.006 mm, depth: 0.5 mm) |
| Filter area: | 10.7 cm² |

Result

The clear filtrate contains no detectable cell mass and has a viscosity at 20° C. and $D=9s^{-1}$ of 738 mPas and a homoglucan content of 10.0 g/l, corresponding to a homoglucan loss in the filtration of 2.14% by weight. The filtration rate is 5300 l/m² h.

EXAMPLE 2

Single-stage pressure filtration of a viscous, homogeneous cell suspension

An inhomogeneous aqueous cell suspension obtained by culturing of *Sclerotium rolfsii* ATCC 15 205 is mechanically homogenized, the result being a cell size distribution ranging in diameter from 0.002 to 0.005 mm.

| | |
|---|---|
| Cell dry matter: | 2.38 g/l |
| Homoglucan content of aqueous solution: | 2.93 g/l |
| Viscosity of cell suspension: | 420 mPas at a shear rate $D = 9s^{-1}$ at 20° C. |

1 liter of this homogeneous cell suspension is introduced into the pressure filter unit shown in the drawing and subjected to a pressure filtration at 20° C. under a positive pressure of 4 bar.

Filter structure

| | |
|---|---|
| Filter stage 2: | Polyurethane foam (density: 60 kg/m³, pore width: 0.25 mm, depth: 50 mm) |
| Filter area: | 10.7 cm² |

Result

Slightly opalescent filtrate having a cell particle dry matter content of 0.013% by weight. The filtrate has a viscosity at 20° C. and $D=9s^{-1}$ of 110 mPas and a homoglucan content of 2.15 g/l, corresponding to a homoglucan filtration loss of 26.6% by weight. The filtration rate is 1703 l/m² h.

EXAMPLE 3

Two-stage pressure filtration of a viscous, homogeneous cell suspension

A viscous, aqueous cell suspension obtained by culturing *Sclerotium glucanicum* CBS 52071 in a vented, mechanically stirred 50 l bioreactor has the following composition:

homogeneous cell size distribution of 0.002 mm (mycelium fragment total) in diameter

| | |
|---|---|
| cell dry matter: | 0.81 g/l |
| homoglucan content: | 4.5 g/l |
| viscosity of cell suspension: | 380 mPas at a shear rate $D = 9s^{-1}$ at 20° C. |

1 liter of this cell suspension is introduced into the pressure filter unit shown in the drawing and subjected to a pressure filtration at 60° C. under a positive pressure of 2 bar.

Filter structure

| | |
|---|---|
| Filter stage 2: | Polyurethane foam (density: 60 kg/m³, pore width: 0.55 mm, depth: 50 mm) |
| Filter stage 3: | Silk gauze (pore width: 0.006 mm, depth: 0.5 mm) |
| Filter area: | 10.7 cm² |

Result

The clear filtrate contains no detectable cell mass and has a viscosity at 20° C. and $D=9s^{-1}$ of 129 mPas and a homoglucan content of 4.23 g/l, corresponding to a homoglucan loss in the filtration of 0.48% by weight. The filtration rate is 8972 l/m² h.

EXAMPLE 4

Two-stage pressure filtration to separate glass milling balls from cell fragments and viscous filtrate 60 g of moist cell mass of the fungus strain *Sclerotium glucanicum* are suspended together with 50 ml of glass milling balls (diameter 0.25 mm) in 140 ml of water and ball-milled to disrupt the cells. The glass milling balls are separated from the suspension of disrupted cells under the following conditions:

Filter structure

| | |
|---|---|
| Filter stage 2: | Polyurethane foam (density: 60 kg/m³, pore width: 0.55 mm, depth: 55 mm) |
| Filter stage 3: | Silk gauze (pore width: 0.05 mm, depth: 0.5 mm) |
| Filter area: | 10.7 cm² |
| Filtration pressure: | 1 bar positive pressure |

Result

The glass milling balls are retained quantitatively in the filter system, while the filtrate contains over 96% by weight of the cell detritus.

EXAMPLE 5

Two-stage pressure filtration for separating an aqueous bacterial suspension 2 liters of an aqueous suspension of *Streptomyces olivacens* having a cell dry matter content of 2.5% is flocculated by crosslinking with glutardialdehyde to give an average floc diameter of from 0.2 to 2.0 mm. From this floc suspension the bacterial flocs are separated quantitatively using the following filter structure:

Filter structure

| | |
|---|---|
| Filter stage 2: | Polyurethane foam (density: 60 kg/m$^3$, pore width: 0.55 mm, depth: 55 mm) |
| Filter stage 3: | Silk gauze (pore width: 0.1 mm, depth: 0.5 mm) |
| Filter area: | 10.7 cm$^2$ |
| Filtration pressure: | 2 bar positive pressure |

Result

The clear filtrate contains no detectable cell mass.

We claim:

1. A process for separating solid particles of various sizes from viscous liquids by pressure filtration whereby solid particles of various sizes are retained, according to size, in superposed or juxtaposed filter stages (1), (2) and (3) on filter layers of various depths and on filter surfaces comprising subjecting an inhomogeneous or a homogenized suspension to pressure filtration thereby separating solid particles according to size in a filter stage (1) comprising a filter layer of a 3-dimensional network of a metal wire, synthetic cloth or a cellulose material having an average pore width of from 1 to 3 mm, in a filter stage (2) comprising a filter layer of an open-pored polyurethane foam having an average pore width of from 0.2 to 0.8 mm and in a filter stage (3) comprisinga filter cloth of natural or synthetic material having a pore size of from 0.006 to 0.2 mm from the viscous liquid.

2. The process of claim 1, wherein silk gauze is used as the filter cloth of filter stage (3).

3. The process of claim 1, wherein a positive pressure of from 1 to 10 bar is used.

4. The process of claim 1, wherein the solid particles are separated from the viscous liquid at a temperature of the suspension of from 20° C. to 60° C.

5. The process of claim 1, wherein the solid particles are separated from a mechanically homogenized cell suspension having a cell size distribution of from 0.002 to 0.005 mm average diameter.

6. The process of claim 1, wherein the solid particles are separated from an inhomogeneous cell suspension containing hypae fragments of from 0.005 mm to 1 cm and having a mycelium content of up to 10 g of dry matter/l, a high polymer concentration of up to 12 g of dry matter/l or both.

7. The process of claim 6, wherein filterability is brought about by adding a small amount of aqueous solution.

8. The process of claim 1, wherein the solid particles are separated from a cell suspension having a viscosity of up to 1200 mPas at a shear rate of about $D=9s^{-1}$ at 20° C.

9. The process of claim 1, wherein the filter stage depths are from 10 to 100 mm in filter stage (1) from 10 to 100 mm in filter stage (2) and 0.5 mm in filter stage (3).

10. The process of claim 9, wherein the depth of filter stage (2) is reduced if filtration is carried out in the presence of filter stage (1).

11. The process of claim 1, wherein filter stage (2) comprises a polyurethane foam of from 60 to 80 kg/m$^3$ in density.

12. The process of claim 1, wherein the pore width of the polyurethane foam is variably reduced in size by compression.

13. The process of claim 1, wherein filtration in filter stages (2) and (3) is carried out with such pore widths so as to produce a clear viscous filtrate.

14. The process of claim 1, wherein the filtration is carried out with such pore widths that the filtration rate is from 5,000 to 10,000 l/m$^2$h.

15. The process of claim 1, wherein viscous suspensions of fungus strains are filtered.

16. The process of claim 15, wherein said viscous solution to be filtered is obtained by culturing fungus strain *Sclerotium rolfsii* ATCC 15 205 or *Silerotium glucanicum* CBS 52 071.

17. The process of claim 1, wherein solid particles are separated from viscous suspensions of celluloid, cellulose ethers, cellulosic fibers, fats, oil, gelation, natural and synthetic resins, adhesives, sealants, pectins, starch, lubricants or polysaccharides from agar, alginate, carregeen or dextran.

18. The process of claim 1, wherein to avoid or reduce filtration losses, one or more wet blankets of aqueous solution are applied to the filter materials of the filter stages, and a dilute solution of the filtrate is isolated and used for slightly diluting the suspension or for culturing microorganisms.

19. A process for separating solid particles of various sizes from viscous liquids by pressure filtration whereby solid particles of various sizes are retained, according to size, in superposed or juxtaposed filter stages (2) and (3) on filter layers of various depths and on filter surfaces comprising subjecting an inhomogeneous or a homogenized suspension to pressure filtration and separating solid particles according to size in a filter stage (2) saccording to size in a filter stage (2) comprising a filter layer of an open-poured polyurethane foam having an average pore width of from 0.2 to 0.8 mm and in a filter stage (3) comprising a filter cloth of natural or synthetic material having a pore size of from 0.006 to 0.2 mm from the viscous liquid.

20. The process of claim 19, wherein a homogeneous suspension of particles in the viscous liquid is prepared in a preliminary stage by means of milling bodies in a milling system and thereafter the milling bodies are separated in filter stage (2) and thereafter in filter stage (3), from the homogeneous phase.

21. The process of claim 20, wherein, following filter stage (3), the homogeneous phase is separated into solid particles and clear viscous liquid in a filter stage (3a) using silk gauze having a pore size smaller than that of the silk gauze of filter stage (3).

22. The process of claim 19, wherein in a preliminary stage an aqueous bacterial suspension is flocculated by crosslinking to an average floc diameter of from 0.2 mm to 2 mm and thereafter the resulting bacterial flocs are separated from the flocculated suspension in filter stage (2) and in filter stage (3).

23. The process of claim 22, wherein the bacterial suspension in flocculated by crosslinking with glutardialdehyde the pore width of the polyurethane foam of filter stage (2) is 0.55 mm and the pore width of the silk gauze of filter stage (3) is 0.1 mm.

* * * * *